United States Patent
Durán et al.

(10) Patent No.: US 6,184,992 B1
(45) Date of Patent: Feb. 6, 2001

(54) APPARATUS AND METHOD FOR MEASURING FLYING HEIGHT AND A REAL INDEX OF REFRACTION

(75) Inventors: Carlos A. Durán, San Diego; Rui-Fang Shi, Carlsbad, both of CA (US)

(73) Assignee: Phase Metrics, Inc., San Diego, CA (US)

( * ) Notice: Under 35 U.S.C. 154(b), the term of this patent shall be extended for 0 days.

(21) Appl. No.: 09/248,164

(22) Filed: Feb. 9, 1999

(51) Int. Cl.[7] .......................... G01B 11/02; G01N 21/41; G01N 21/43
(52) U.S. Cl. ............................................. 356/507; 356/517
(58) Field of Search .................... 356/361, 397, 356/358

(56) References Cited

U.S. PATENT DOCUMENTS

| | | | |
|---|---|---|---|
| 4,606,638 | * 8/1986 | Sommargren | 356/351 |
| 5,218,424 | * 6/1993 | Sommargren | 356/358 |
| 5,280,340 | 1/1994 | Lacey . | |
| 5,457,534 | 10/1995 | Lacey et al. . | |
| 5,557,399 | * 9/1996 | De Groot | 356/357 |
| 5,644,562 | 7/1997 | de Groot . | |
| 5,663,793 | * 9/1997 | De Groot | 356/351 |
| 5,781,299 | * 7/1998 | Womack et al. | 356/357 |
| 5,793,480 | * 8/1998 | Lacey et al. | 356/73 |

* cited by examiner

Primary Examiner—Robert H. Kim
Assistant Examiner—Phil Natividad
(74) Attorney, Agent, or Firm—Irell & Manella LLP

(57) ABSTRACT

An apparatus that can measure a space between a first surface and a second surface. The apparatus may include a light source that can reflect a light beam from the first and second surfaces. A birefringent element may split the reflected light beam into an ordinary beam and an extraordinary beam. The ordinary and extraordinary beams are detected by a photodetector. The apparatus may include a controller that is coupled to the photodetector and which can compute the space from a phase value that is determined from data collected when the mechanism varies the phase between the ordinary and extraordinary beams, and a ratio between a first modulation amplitude detected from light reflected from the first and second surfaces and a second modulation amplitude detected from light reflected from the first surface when the second surface is not adjacent to the first surface. The ratio can also be used to compute the reflectance and index of refraction of the second surface. This method thus allows the space to be computed without performing a separate measurement to determine the index of refraction.

10 Claims, 3 Drawing Sheets

APPARATUS AND METHOD FOR MEASURING FLYING HEIGHT AND A REAL INDEX OF REFRACTION

BACKGROUND OF THE INVENTION

1. Field of the Invention

The present invention relates to an optical apparatus such as a flying height tester for determining a flying height and the modulus of the index of refraction of a slider that is separated from a disk.

2. Background Information

Hard disk drives contain magnetic transducers which write and read information onto a rotating magnetic disk(s). The transducers are typically integrated into a slider that is assembled to a flexure arm. Some sliders contain a transducer to write information and a separate transducer to read information. The read transducer may be constructed from a magneto-resistive (MR) material. The slider and arm are commonly referred to as a head gimbal assembly (HGA). Each HGA is attached to an actuator arm that can move the sliders across the surfaces of the disk(s).

Each slider has an air bearing surface which cooperates with an air flow generated by the rotating disk(s) to create an air bearing between the disk and the transducer. The air bearing prevents mechanical wear between the slider and the disk surface. It is desirable to minimize the length of the space which separates the transducer and the disk to maximize the magnetic coupling between the two components. Sliders are therefore designed to create an optimal space between the transducer and the disk.

It is desirable to measure the thickness of an air bearing created by a slider. The thickness, or "flying height," is typically measured with an optical system that places a slider adjacent to a rotating transparent disk. A light beam is then directed through the transparent disk and reflected from the slider back to a photodetector. The detected light is used to compute the flying height of the slider. The current industry standard is the Dynamic Flying Height Tester (DFHT) sold by Phase Metrics, Inc. the assignee of the present application. The DFHT utilizes multiple wavelength intensity based interferometry to determine the flying height. The operation of the DFHT is discussed in U.S. Pat. No. 5,280,340 issued to Lacey, and U.S. Pat. No. 5,457,534 issued to Lacey et al.

The transducers may be fabricated by depositing thin films of material onto a wafer substrate constructed from AlTiC. A final capping layer of $Al_2O_3$ is deposited to protect the transducer. The wafer is then sliced into individual slider elements such that the air bearing surface is primarily AlTiC material. The AlTiC air bearing surfaces may be further covered with a protective coating of diamond-like carbon (DLC).

The sliders may have rails located along an air bearing surface which assist in creating the air bearing. The transducers are located at the trailing edge of the rails. The sliders typically "fly" at an oblique angle relative to the disk so that the transducers are closer to the disk surface than most of the surface of the rails.

Flying height testers are typically operated so that the light beam is reflected from the rails of the slider. Unfortunately this does not provide an accurate measurement of the distance between the disk and the transducer located at the trailing edge of the slider. As discussed in an article by Yufeng Li, ASME/STLE Joint Tribology Conference, San Francisco, Calif., Oct. 13–17, 1996, it is desirable to direct the light beam onto the $Al_2O_3$ cap of the transducer to evaluate the tribological and magnetic performance of the slider.

AlTiC is a granular material which may have varying grain sizes throughout the air bearing surface. The non-uniform grain sizes can vary the optical properties at different locations of the air bearing surface. To accurately determine the flying height, the DFHT must be calibrated to compensate for changes in optical properties. The DFHT is calibrated by moving the slider away from the disk and recording data.

The DFHT has a loader which places the slider adjacent to the disk. The loader pivots between a load position and an unload position. The pivotal movement of the slider during the calibration routine introduces a rotation which may change the location on the slider from which the light beam is being reflected. Unfortunately, the new location may have a different optical property that will degrade the accuracy of the calibration routine and the measurements by the flying height tester.

This problem becomes particularly acute when trying to measure the $Al_2O_3$ cap. $Al_2O_3$ has optical properties which are different than the optical properties of AlTiC. Therefore movement of the light beam from $Al_2O_3$ to AlTiC during the calibration routine may create an inaccurate calibration and incorrect flying height measurements because of the drastic change in optical properties. It would therefore be desirable to provide a flying height tester which can accurately measure at the $Al_2O_3$ cap of a hard disk drive slider.

The DFHT utilizes algorithms that are dependent upon the complex index of refraction (n and k), which is an optical property of the slider material. The complex index of refraction for each batch of sliders is typically measured with an ellipsometer and stored in the DFHT for use in computing the flying height. Having to separately determine the complex index of refraction is time consuming and thus increases the cost of testing the sliders and mass producing hard disk drives.

There has been marketed a flying height tester by Zygo Corp. under the trademark PEGASUS 2000 FHT which determines both the complex index of refraction and the flying height of a slider. The Zygo machine is further explained in U.S. Pat. No. 5,557,399 issued to DeGroot. The Zygo machine utilizes a polarized light beam that is reflected from the disk and the slider at an oblique angle. The approach implemented in the Zygo machine has the following problems.

It is difficult to analyze a polarized beam that is reflected from a spinning glass disk. The centrifugal forces generate stresses which make the glass birefringent. Birefringence is a characteristic of some materials that can be described as if the material had different indices of refraction depending on the polarization state of the light. In the context of Polarization-based FHTs, such as the Zygo machine, it means that the polarization states of both the probing beam and of the reflected beam that carries the information on flying height are changed as they travel through the glass disk. These effects are of such magnitude in regular flying height testing conditions that they render the measurements meaningless if they are not corrected. A complex correction method for the Zygo machine is described in U.S. Pat. No. 5,644,562, issued to De Groot.

The requirement for oblique incidence poses difficulties when it comes to accurately positioning the measurement spot on the surface of the slider. The Zygo machine requires a compromise between either determining the spot position from a low quality, high angle perspective, or necessitates an extra normal incidence view channel that must be precisely registered to the oblique measurement channel. This registration is susceptible to mechanical drift and in addition needs to be redone every time the transparent disk is changed, a task that is regularly performed in mass testing environments.

Additionally, even though the three unknowns of flying height testing, flying height, and the components of the complex index of refraction n and k, are independent variables, they are closely coupled in the ellipsometric-type model that is used in the Zygo machine to interpret the data, resulting in solutions that are naturally unstable and tend to produce correlated fluctuations in the flying height and complex index of refraction.

Another problem in measuring flying heights is the granular nature of the AlTiC slider material. When a beam of light impinges on the slider surface, it is not cleanly reflected in a specular fashion. Instead, a large fraction of the light is scattered off in a diffuse manner, and even the portion of the light that reflects specularly gets significantly depolarized. It is extremely difficult to properly account for these effects in the theoretical model that is used for analyzing the data, since all the common approximations break down in the regime in which the grain size is of the order of the wavelength of the light. This results in having to introduce other ad hoc correction factors, such as what percentage of the light actually makes it back to the detector after reflection, and what fraction of the detected light retains the polarization information required to determine the flying height.

The DLC coating of the air bearing surface introduces yet another problem. An error in the flying height measurement is introduced in the Zygo machine since the model interprets the various reflections from the different interfaces within the material as a single reflection, caused by an average material, located at a certain depth beneath the actual surface. This effect appears also at normal incidence, but for DLC-coated AlTiC its magnitude is close to a factor of 5 times smaller at normal incidence that at angles between 45 and 60 degrees used in the Zygo machine. The effect is important if the indices of refraction of the substrate (AlTiC in this case), and the coating (DLC) are very different.

There has also been developed a flying height tester by the assignee of the present application, Phase Metrics, Inc., which is disclosed and claimed in application Ser. No. 09/248,182 filed in the name of Duran, et al. In the Duran application a birefringent element such as a Savart plate is used to split the light reflected from the slider/disk interface into an ordinary beam and an extraordinary beam, thereby creating a double image of the slider/disk interface. A photodetector detects an interference pattern of the beams. A mechanism is provided to move the reflected light relative to the Savart plate so that a phase value $\emptyset$ can be computed. The flying height h can then be determined from the phase value $\emptyset$.

FIG. 1 shows a vector representation of the light reflected from the slider/disk interface. The term $R_g$ is the reflectance of the disk and is a known value. $R_s$ is the reflectance of the slider and is a function of the real index of refraction of the $Al_2O_3$ cap material. FIG. 1 illustrates the case when $R_s < R_g$, which is particularly important since it gives rise to ambiguity in the determination of α from φ. The phase angle $\emptyset$ is measured in accordance with the "Savart" technique described in the Duran application. The flying height h can be determined from the phase angle α in accordance with the following equation.

$$\alpha = \frac{4\pi h}{\lambda} \quad (1)$$

where;

λ=the wavelength of the reflected light.

The term $R_t$ is the total reflectance and is an unknown value when using the Savart technique. Because $R_t$ is unknown the phase angle α can be one of two values $\alpha_1$ or $\alpha_2$ for the same phase angle $\emptyset$. Assuming an incorrect value for α will produce inaccurate test results.

It would be desirable to provide a flying height tester which can accurate measure the distance between a disk and a slider without employing a separate tester such as an ellipsometer to compensate for varying reflectances of the slider, and that can remove the ambiguity in the determination of α shown in FIG. 1.

SUMMARY OF THE INVENTION

One embodiment of the present invention is an apparatus that can measure a space between a first surface and a second surface. The apparatus may include a light source that can reflect a light beam from the first and second surfaces. A birefringent element may split the reflected light beam into an ordinary beam and an extraordinary beam which have a phase relative to each other. An interference between the ordinary and extraordinary beams is detected by a photodetector. The apparatus may include a controller that is coupled to said photodetector and which can compute the space from a phase value that is determined from data collected when the relative phase between the ordinary and extraordinary beams is varied. The controller may also compute and utilize a ratio between a first modulation amplitude detected from light reflected from the first and second surfaces and a second modulation amplitude detected from light reflected from the first surface when the second surface is not adjacent to the first surface. The ratio can be used to calculate the space and the real index of refraction of the second surface.

DETAILED DESCRIPTION

One embodiment of the present invention is an apparatus that can measure a space between a first surface and a second surface. The apparatus may include a light source that can reflect a light beam from the first and second surfaces. A birefringent element may split the reflected light beam into an ordinary beam and an extraordinary beam which have a phase relative to each other. An interference between the ordinary and extraordinary beams is detected by a photodetector. The apparatus may include a controller that is coupled to the photodetector and which can compute the space from a phase value that is determined from data collected when the relative phase between the ordinary and extraordinary beams is varied. The controller may also compute and utilize a ratio of a first modulation amplitude detected from light reflected from the first and second surfaces and a second modulation amplitude detected from light reflected from the first surface when the second surface is not adjacent to the first surface. The ratio can also be used to compute the reflectance and index of refraction of the second surface when the index of refraction of the first surface is known. This method thus allows the space to be computed without performing a separate measurement to determine the index of refraction.

Figure 2:
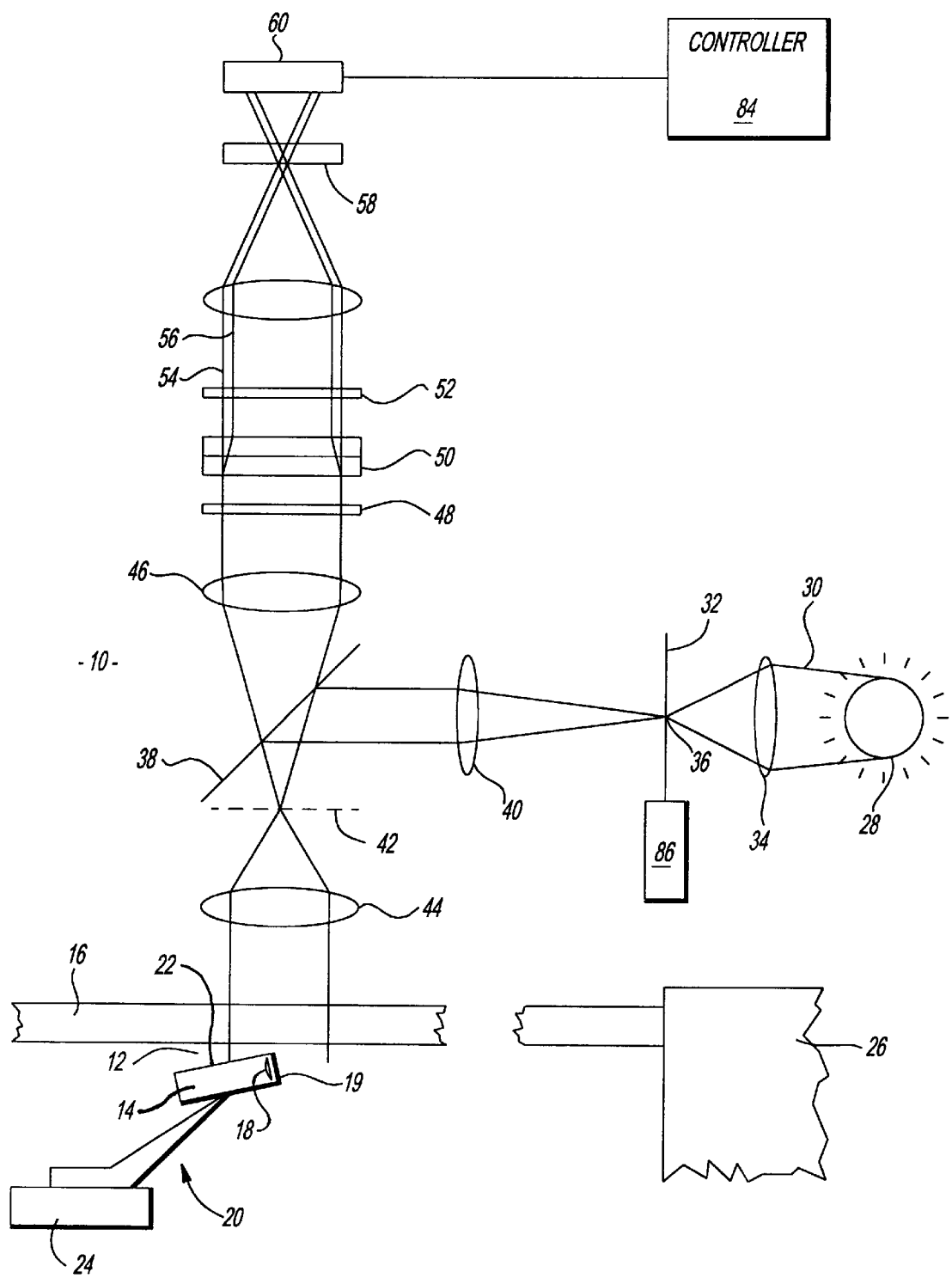
FIG. 2 is a schematic of an embodiment of an apparatus of the present invention.

Referring to the drawings more particularly by reference numbers, FIG. 2 shows an embodiment of an apparatus 10 of the present invention. The apparatus 10 may be a flying height tester which measures the space 12 between a slider 14 and a rotating transparent disk 16. Generally, the disk 16 may be described as a first surface and the slider 14 may be described as a second surface. The slider 14 may have a transducer 18 that is covered with an $Al_2O_3$ cap 19. The remaining portion of the slider 14 may be constructed from AlTiC material.

The slider 14 is typically integrated into a head gimbal assembly (HGA) 20 which is eventually assembled into a hard disk drive. The apparatus 10 can be used to measure a space such as an air bearing "flying height" that is formed by an air bearing surface 22 of the slider 14 and an air flow created by the rotating disk 16. The apparatus 10 may have a loader 24 that can retain the HGA 20 and place the slider 14 adjacent to the disk 16. An operator of the apparatus typically replaces the HGA 20 with another part after the flying height has been measured. The transparent disk 16 is rotated by a motor 26 that is integrated into a spindle stand.

The apparatus 10 may include a light source 28 that generates a light beam 30 which is focused onto an aperture 32 by a lens 34. The light beam 30 passes through a slit 36 of the aperture 32. The lens 40 focuses the light beam in a manner to form an image of the slit 36 at or close to the back focal plane 42 of lens 44, after reflecting off a beamsplitter 38. Lens 44 directs a substantially partially collimated light beam onto the disk 16 and slider 14. By partially collimated we mean a light beam that includes rays that are restricted to travel in a plane of collimation. The plane of collimation may include the optical axis and a direction substantially parallel to the trailing edge of the slider 14.

The partially collimated light is reflected from the disk 16 and the slider 14. The light is reflected through the beamsplitter 38 and lens 46. The lens 46 has a focal point located at the back focal plane 42 of lens 44.

The lens 46 directs the light through a first polarizer 48, a birefringent element 50 and a second polarizer 52. The polarizer 48 may be either parallel or perpendicular to the plane of collimation. The light beam that emerges from the polarizer 48 may thus have components linearly polarized at plus and minus 45° from the plane of collimation, although it is to be understood that the beam may have components polarized at angles greater or less than 45°.

The birefringent element 50 splits the polarized light beam into an ordinary beam(s) 54 and an extraordinary beam(s) 56 which have a phase relative to each other. In essence the element 50 creates a double image of the disk 16 and the slider 14. The birefringent element 50 may be a Savart plate which contains two substantially equal pieces of birefringent material such as calcite or quartz that are cut at a crystalline direction and attached to each other. A Savart plate suitable for the present invention can be purchased from Karl Lambrecht Corp. of Chicago Ill.

Savart plates provide minimal retardation so that the ordinary 54 and extraordinary 56 beams can interfere to form an interference pattern. Although a Savart plate is shown and described, it is to be understood that other birefringent elements may be used in the present invention. For example, a single birefringent element may be used, particularly if the light source is a laser or laser diode.

In a technical sense, the outcoming beams of a Savart plate cannot be called "ordinary" and "extraordinary." Since the Savart plate consists of two pieces of birefringent material, the initial pair of ordinary beam and extraordinary beam switch places when they enter the second piece of material, respectively becoming extraordinary and ordinary. This application will, nevertheless, use the names ordinary and extraordinary in an ample way to include cases involving a single piece of birefringent material.

The ordinary 54 and extraordinary 56 beams are made to interfere with each other by polarizer 52, filtered by a color filter 58 and detected by a photodetector 60. The photodetector 60 may be a charge coupled device (CCD) camera which contains a plurality of individual pixels arranged in a two dimension array. The photodetector 60 detects the interference pattern of the ordinary 54 and extraordinary 56 beams.

Figure 1:
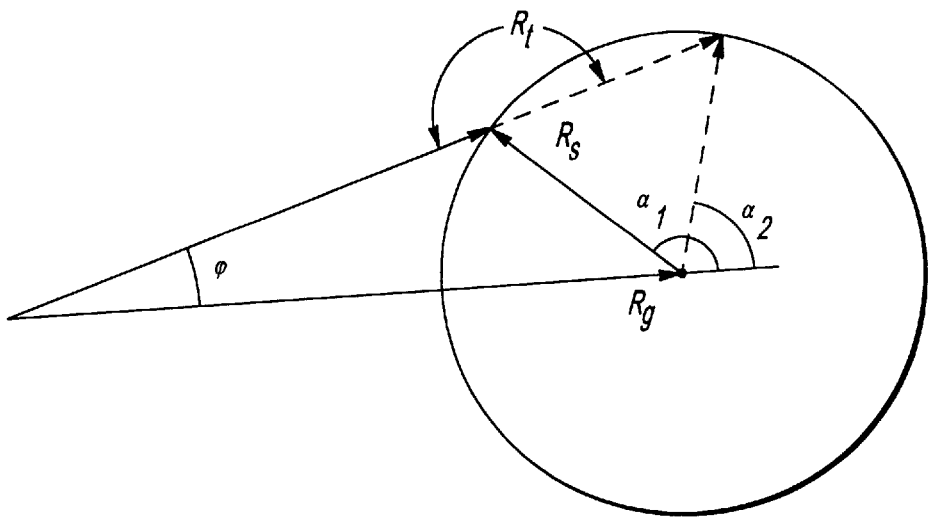
FIG. 1 is a vector diagram showing the relative intensities of interfering light in a flying height tester.
Figure 3:
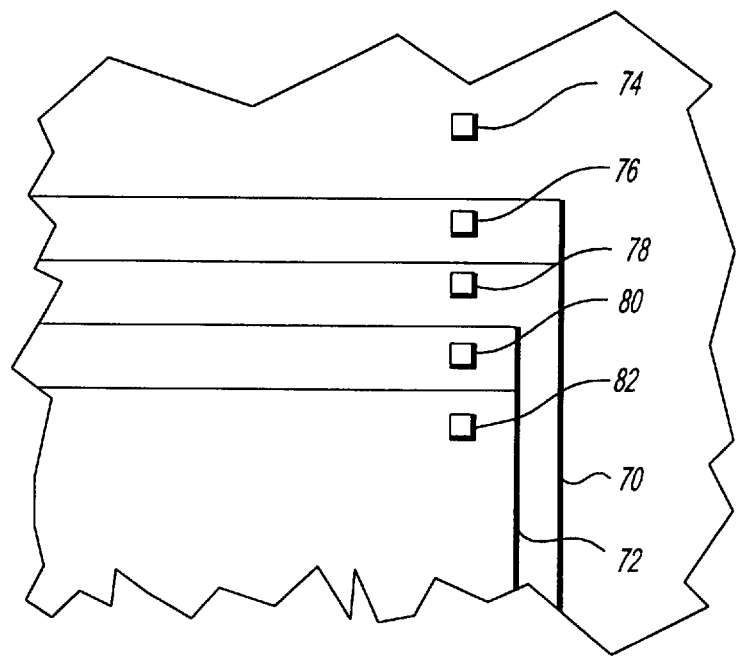
FIG. 3 is a bottom view of a double image on a photodetector.

FIG. 3 shows the double image 70 and 72 on the photodetector. The distance between the images 70 and 72 is referred to as a shear which has a corresponding shear direction. The shear direction is dictated by the orientation of the Savart plate. The orientation of the Savart plate also determines the orientation of the polarizers and slit.

The photodetector may have a number of pixels 74, 76, 78, 80 and 82, or groups of pixels, which sense different modulations of the interfering light. For example, pixel 74 will sense light only reflected from the disk. Pixel 76 will sense light that is reflected from the slider/disk interface at the location of the $Al_2O_3$ cap as provided in image 70, and light reflected from just the disk as provided by image 72. Pixel 78 may sense light that is reflected from the slider/disk interface at the location of the AlTiC material as provided by image 70, and light reflected from just the disk as provided by image 72. Pixel 80 may sense light that is reflected from the slider/disk interface at the location of the $Al_2O_3$ cap as provided by image 72, and light reflected from the slider/ disk interface at the location of the AlTiC material as provided by image 70. Finally, pixel 82 may sense light that is reflected from the slider/disk interface at a location of the AlTiC material as provided by images 70 and 72.

It being understood that the light reflected from the slider/disk interface contains phase information that can be related to the flying height in accordance with the following equations.

$$\theta = \arctan[R_s R_g \sin(\delta)/\{1-R_s R_g \cos(\delta)\}] - \arctan[R_s \sin(\delta)/\{R_g - R_s \cos(\delta)\}] \quad (1)$$

$$\delta = 4\pi h/\lambda \quad (2)$$

where;

$\theta$ = a measured phase value;

h = the flying height;

$R_g$ = the reflectance of the glass-air interface, which can be predetermined;

$R_s$ = the reflectance of the air-slider interface which is defined by the equation $(n-1)/(n+1)$ and can be computed or predetermined, n being the real index of refraction of the slider;

λ=the wavelength of the reflected light.

Referring to FIG. 2, the photodetector 60 can be coupled to a controller 84. The photodetector 60 may provide electrical data signals which are a function of the measured intensity of the reflected light. The controller 84 may be a computer which has a microprocessor, memory, interface circuits, etc., which can receive the data signals from the detector 60 and perform software algorithms to determine different variables including the phase value ∅ and flying height h.

Figure 4:
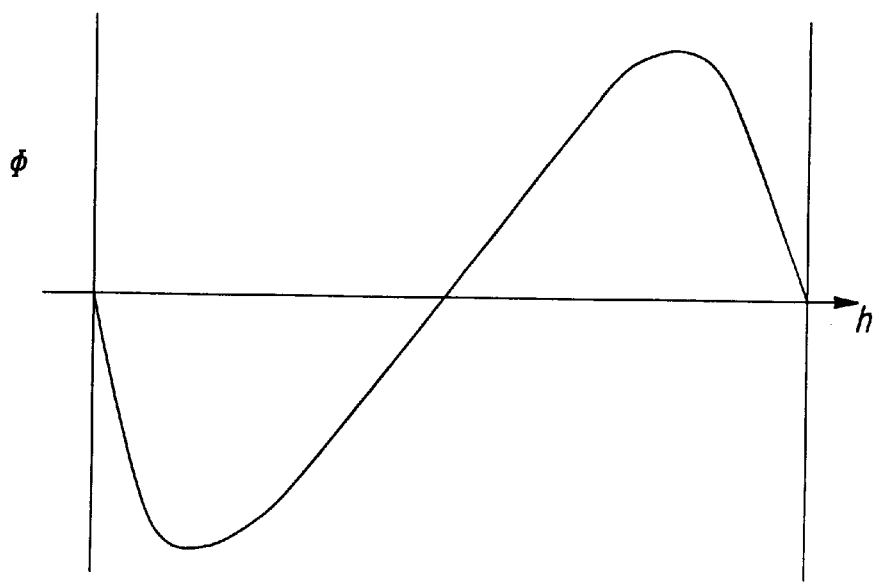
FIG. 4 is a graph showing a correlation between a phase value and a flying height.

When measuring the flying height between the $Al_2O_3$ cap and the disk, data from pixel 76 shown in FIG. 3, can be used to calculate the phase value ∅ and the flying height h. The controller 84 can receive the data from the detector and determine the phase value ∅. The controller 84 can then utilize equations (1) and (2) to compute the flying height h from the measured phase value ∅. A graph showing the correlation between the phase value ∅ and the flying height h is shown in FIG. 4.

The phase value ∅ can be measured in accordance with a technique that is discussed in "Temporal Phase Measurement Methods", by K. Creath, in Interferogram Analysis: digital fringe pattern measurement techniques, Ed. D. W. Robinson and G. T. Reid, IOP Publishing Ltd. London (1993). This technique requires a recordation of a succession of slider/disk images at regular changes in phase retardation.

The relative phase retardation of the ordinary and extraordinary beams can be varied by tilting the incoming beam relative to the Savart plate. The relevant tilt can be accomplished by moving the beam in a plane defined by the optical axis and the shear direction of the system. In one embodiment, the light beam is tilted by moving the aperture 32 with a mechanism 86 shown in FIG. 2. Alternatively, the image of the slit can be moved by a glass plate (not shown) that is located between the slit 36 and lens 40 and is tilted by a mechanism. As another embodiment, the Savart plate can be tilted by a mechanism.

A minimum of three images are required to obtain the phase value ∅, although it is to be understood that a larger number of frames can be taken. In one embodiment, seven frames are taken to determine the phase value ∅.

The phase measured at pixel 76 will differ from the true value of ∅ by a constant that will depend on a number of factors such as the particular arrangement of the optical components, and the starting point of the phase shifting used to determine the phases. The constant can be determined by performing a phase measurement at the same pixel of the detector when the slider is not adjacent to the disk. This can be done either by mechanically displacing the slider out of the view of the pixel, or measuring the light intensity at the pixel before the slider is loaded onto the disk. The second approach is preferred due to performance considerations.

The phase value constant is affected by thermal drifts in the apparatus, so it tends to change over time, and needs to be updated every few minutes to insure accurate measurements. In the preferred embodiment in which detector 60 is an image detector, a time evolution at picture element 74 can be used for correcting the drift, enabling accurate measurements to be taken for periods of hours without constantly performing the phase value constant calibration. Also, for a perfect system in which the additive phase is constant throughout the entire field of view, the phase measured at picture element 76 can be referenced to the phase measured at picture element 74. In one embodiment, the expression $$\emptyset_{76c} = \emptyset_{76} - \emptyset_{76G} - (\emptyset_{74} - \emptyset_{74G}) \quad (3)$$

can be used to correct for both spatial and temporal variations of the phase. $\emptyset_{76}$ and $\emptyset_{74}$ are the phases respectively measured at pixels 76 and 74 when the slider is loaded adjacent to the disk, while $\emptyset_{76G}$ and $\emptyset_{74G}$ are the phase values measured at the same detector locations when the slider is not adjacent to the disk. $\emptyset_{76c}$ is the corrected phase value to be used in the flying height determination of Equations (1) and (2).

For high speed dynamic measurements, the detector 60 may be a line scan camera or a fast photodetector containing a few detector elements. An initial measurement is performed similarly to the area detector measurements previously described. Then the phase shift is preferably adjusted to yield an intensity reading on the detector close to the center of the range of intensities to get high sensitivity, and intensities are then recorded at high speed to obtain the desired dynamic information. Alternatively, the fast streams of data are gathered at each different phase shift. The average spacing is determined with high accuracy from the averages of the data streams, and the data stream or streams with the highest sensitivity are then used to evaluate the dynamic behavior.

The index of refraction n of the material from which the light beam is reflected can be separately measured by an ellipsometer and stored in the controller 84 for later use in determining the flying height with equations (2) and (3). As an alternate embodiment the reflectance of the slider $R_s$, which is a function of the index n, and the flying height h can be computed with the following equations.

$$h = \left\{\arctan\left[\frac{R_g(1+R_s^2)+(1+R_g^2)y}{(1-R_g^2)y}\tan\phi\right]+\pi\right\}\frac{\lambda}{4\pi}, \quad (5)$$

$$y = \{(-1+m^2R_g^4)[1-m^2R_g^2+m(-1+R_g^2)\sec\phi] - \quad (6)$$

$$[1+m^4R_g^6+m^2R_g^2(1+R_g^2)]\tan^2\phi\} \times$$

$$\frac{R_g\cos^2\phi}{1+m^4R_g^8-2m^2R_g^4\cos2\phi}$$

where;

m=is a normalized modulation amplitude, which is a ratio between a measured first modulation amplitude of the slider/disk interface and a measured second modulation amplitude of only the disk without a slider;

$$R_s = \sqrt{\frac{R_g[R_g(1-m^2)+2y(1-m^2R_g^2)]}{-1+m^2R_g^4}}, \quad (7)$$

Figure 5:
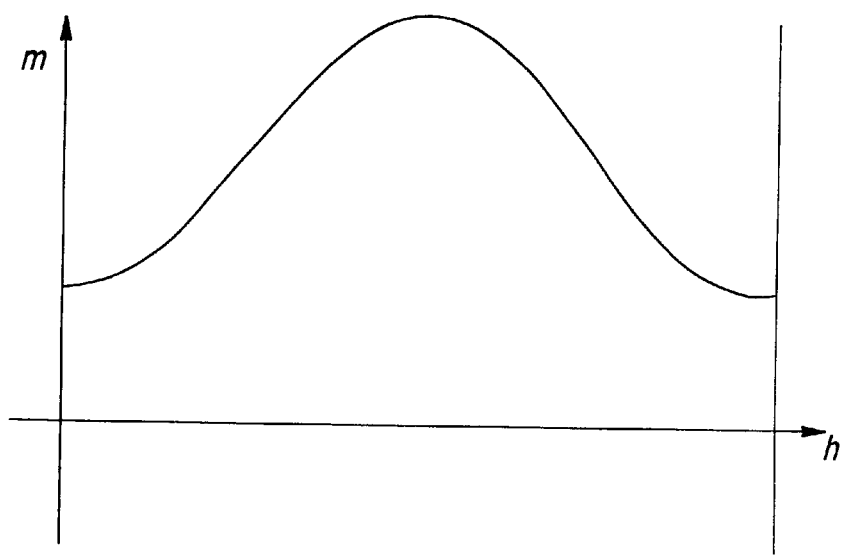
FIG. 5 is a graph showing a correlation between a normalized modulation amplitude and the flying height.

To obtain the normalized modulation amplitude m the first modulation amplitude at pixel 76 can be measured when a slider is not adjacent to the disk. By way of example, this measurement can be performed when the operator is replacing the HGA. The slider is then loaded adjacent to the disk and the apparatus measures the second modulation amplitude of light at pixel 76. The controller can then compute the ratio m. A correlation between m and h is shown in FIG. 5.

The phase value ∅ can be determined with the "Savart" technique described above. With the values m and ∅, the controller can compute the flying height h with equations (5), (6) and (7). The controller can also compute the real index of the slider material with the equation.

$$n = \frac{1+R_s}{1-R_s} \qquad (8)$$

The present invention thus provides an apparatus that can measure a space between a slider and a disk without having to predetermine the real index of refraction of the slider.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. For example, the reference measurements in which the phase and first modulation amplitudes are measured for the first surface only while the second surface is not present could be replaced by measurement on a surrogate surface of properties similar to those of the first surface in applications in which separating the first and second surfaces is impractical.

Although measurements of flying height at the Al$_2$O$_3$ cap of the slider, where the index of refraction is real, has been described, it is to be understood that the present invention allows measurements to be performed on the AlTiC portion of the slider as well. This would require the expression for $R_s$ to be rewritten for a material with a complex index of refraction, and the introduction of a correction for the phase shift on reflection, as taught in U.S. Pat. Nos. 5,280,340 and 5,457,534, which are hereby incorporated by reference.

Although the method taught in this application is specifically described in the context of measurements taken with a flying height tester that includes a Savart plate, it should be clear to those skilled in the art that the incorporation of the measurement of a modulation amplitude as a complement to phase measurements has many potential applications. For example, the method could be applied to flying height testers that implement phase shifting interferometry methods in other ways. Outside of flying height testing, it could be applied in optical profilometers based on phase shifting interferometry as an aid in correcting for some types of variations in the optical properties of test samples.

What is claimed is:

1. An apparatus that can measure a space between a first surface and a second surface, comprising:
   a loader that can move the second surface adjacent to the first surface;
   a light source that reflects a light beam from the first and second surfaces;
   a birefringent element that splits the reflected light beam into an ordinary beam and an extraordinary beam which have a phase relative to each other;
   a mechanism which can vary the phase between the ordinary and the extraordinary beams;
   a photodetector which detects the interference between the ordinary and the extraordinary beams at a pixel location;
   a controller that is coupled to said photodetector and which can compute the space from a phase value that is determined from data collected when said mechanism varies the phase between the ordinary and extraordinary beams, and a ratio between a first modulation amplitude detected from light reflected from the first and second surfaces and a second modulation amplitude detected from light reflected from the first surface when the second surface is not adjacent to the first surface, the first modulation amplitude and the second modulation amplitude being detected at the pixel location.

2. The apparatus as recited in claim 1, wherein the space is computed in accordance with an equation $$h = \left\{ \arctan\left[ \frac{R_g(1+R_s^2) + (1+R_g^2)y}{(1-R_g^2)y} \tan\phi \right] + \pi \right\} \frac{\lambda}{4\pi}, \qquad (5)$$

where;

$$y = \{(-1+m^2 R_g^4)[1-m^2 R_g^2 + m(-1+R_g^2)\sec\phi] - \qquad (6)$$
$$[1+m^4 R_g^6 + m^2 R_g^2(1+R_g^2)]\tan^2\phi\} \times$$
$$\frac{R_g \cos^2\phi}{1+m^4 R_g^8 - 2m^2 R_g^4 \cos 2\phi}$$

$$R_s = \sqrt{\frac{R_g[R_g(1-m^2) + 2y(1-m^2 R_g^2)]}{-1+m^2 R_g^4}}. \qquad (7)$$

3. The apparatus as recited in claim 1, wherein said controller also computes a real index of refraction from the ratio.

4. A flying height tester that can measure a space between a slider and a disk, comprising:
   a transparent disk;
   a motor that rotates said transparent disk;
   a loader which can place the slider adjacent to said transparent disk so that the slider and said transparent disk are separated by a space;
   a light source that reflects a light beam from the slider and said transparent disk;
   a birefringent element that splits the reflected light beam into an ordinary beam and an extraordinary beam which have a phase relative to each other;
   a mechanism which can vary the phase between the ordinary and the extraordinary beams;
   a photodetector which detects an interference between the ordinary and extraordinary beams at a pixel location;
   a controller that is coupled to said photodetector and which can compute the space from a phase value that is determined from data collected when said mechanism varies the phase between the ordinary and extraordinary beams, and a ratio of a first modulation amplitude detected from light reflected from the slider and said transparent disk, and a second modulation amplitude detected from light reflected from said transparent disk when the slider is not adjacent to said transparent disk, the first modulation amplitude and the second modulation amplitude being detected at the pixel location.

5. The tester as recited in claim 4, wherein the space is computed in accordance with an equation $$h = \left\{ \arctan\left[ \frac{R_g(1+R_s^2) + (1+R_g^2)y}{(1-R_g^2)y} \tan\phi \right] + \pi \right\} \frac{\lambda}{4\pi}, \qquad (5)$$

$$y = \{(-1+m^2 R_g^4)[1-m^2 R_g^2 + m(-1+R_g^2)\sec\phi] - \qquad (6)$$
$$[1+m^4 R_g^6 + m^2 R_g^2(1+R_g^2)]\tan^2\phi\} \times$$
$$\frac{R_g \cos^2\phi}{1+m^4 R_g^8 - 2m^2 R_g^4 \cos 2\phi}$$

$$R_s = \sqrt{\frac{R_g[R_g(1-m^2) + 2y(1-m^2 R_g^2)]}{-1+m^2 R_g^4}}. \qquad (7)$$

6. The apparatus as recited in claim 4, wherein said controller also computes a real index of refraction from the normalized modulation amplitude.

7. A method for determining a space between a first surface and a second surface, comprising;
   a) reflecting a light beam from the first surface;
   b) detecting the reflected light beam at a pixel location;
   c) determining a first modulation amplitude from the reflected light beam;
   d) moving the second surface adjacent to the first surface;
   e) reflecting a light beam from the first and second surfaces;
   f) detecting the reflected light beam at the pixel location;
   g) determining a second modulation amplitude from the reflected light beam;
   h) computing a ratio of the first modulation amplitude and the second modulation amplitude;
   i) determining a phase value from the reflected light beam; and,
   j) computing the space from the ratio and the phase value.

8. The method as recited in claim 7, further comprising the step of computing a real index of refraction of the second surface with the ratio and the phase value.

9. An apparatus that can measure a real index of refraction between a first surface and a second surface, comprising:
   a loader that can move the second surface adjacent to the first surface;
   a light source that reflects a light beam from the first and second surfaces;
   a birefringent element that splits the reflected light beam into an ordinary beam and an extraordinary beam which have a phase relative to each other;
   a mechanism which can vary the phase between the ordinary and the extraordinary beams;
   a photodetector which detects an interference between the ordinary and extraordinary beams at a pixel location;
   a controller that is coupled to said photodetector and which can compute the real index of refraction from a phase value that is determined from data collected when said mechanism varies the phase between the ordinary and extraordinary beams, and a ratio between a first modulation amplitude detected from light reflected from the first and second surfaces and a second modulation amplitude detected from light reflected from the first surface when the second surface is not adjacent to the first surface, the first modulation amplitude and the second modulation amplitude beings detected at the pixel location.

10. A method for determining a space between a first surface and a second surface, comprising;
   a) reflecting a light beam from the first surface;
   b) detecting the reflected light beam at a pixel location;
   c) determining a first modulation amplitude from the reflected light beam;
   d) moving the second surface adjacent to the first surface;
   e) reflecting a light beam from the first and second surfaces;
   f) detecting the reflected light beam at the pixel location;
   g) determining a second modulation amplitude from the reflected light beam;
   h) computing a ratio of the first modulation amplitude and the second modulation amplitude;
   i) determining a phase value from the reflected light beam; and,
   j) computing the real index of refraction from the ratio and the phase value.

* * * * *